United States Patent [19]

Vanderspurt

[11] 4,224,187
[45] Sep. 23, 1980

[54] OLEFIN OXIDATION CATALYST AND PROCESS FOR ITS PREPARATION

[75] Inventor: Thomas H. Vanderspurt, Homestead Park, N.J.

[73] Assignee: Celanese Corporation, New York, N.Y.

[21] Appl. No.: 960,201

[22] Filed: Nov. 13, 1978

[51] Int. Cl.² ........................ B01J 23/78; B01J 23/84; B01J 23/88; B01J 27/18

[52] U.S. Cl. .................................. 252/437; 252/462; 252/469; 252/470; 568/480

[58] Field of Search ............... 252/437, 469, 470, 462; 260/604 R

[56] References Cited

U.S. PATENT DOCUMENTS

| | | | |
|---|---|---|---|
| 3,778,386 | 12/1973 | Takenaka et al. | 252/437 X |
| 4,001,317 | 1/1977 | Grasselli et al. | 252/470 X |
| 4,040,978 | 8/1977 | Li | 252/437 |

Primary Examiner—W. J. Shine
Attorney, Agent, or Firm—Kenneth A. Genoni

[57] ABSTRACT

This invention provides an improved catalyst for vapor phase oxidation of propylene or isobutylene to the corresponding acrolein or methacrolein product. In a preferred embodiment, the oxidation catalyst corresponds to the formula:

$$Mo_{12}Co_{4.5}Fe_{2.4}Ni_{2.3}Bi_{0.5-2}K_{0.65-1.3}P_{0.35-0.5}O_x$$

This formula further provides a method of preparing the improved oxidation catalyst which in one important aspect of the preparation involves controlling the pH of an aqueous slurry admixture of catalyst components within the range of about 1–5.

6 Claims, No Drawings

OLEFIN OXIDATION CATALYST AND PROCESS FOR ITS PREPARATION

BACKGROUND OF THE INVENTION

Various oxidation catalysts have been proposed for use in a vapor phase catalytic oxidation of olefinically unsaturated hydrocarbons to produce corresponding unsaturated aldehydes with a view of enhancing selectivity for desired unsaturated hydrocarbon without reducing conversion of olefin raw material. The known oxidation catalysts include, for example, cuprous oxide, cupric oxide, bismuth molybdate or bismuth phospho molybdate, cobalt molybdate, antimony oxide, bismuth oxide, vanadium oxide and the like.

U.S. Pat. No. 3,454,630 describes a process for converting propylene and isobutylene to the corresponding unsaturated aldehydes and carboxylic acids in the presence of a catalyst of the elements of Ni, Co, Fe, Bi, P, No, O. In U.S. Pat. No. 3,454,630 propylene is oxidized to acrolein in a maximum single pass yield of 71 percent. In Canadian Pat. No. 781,513 the maximum single pass yield of acrolein from propylene is 75.5 percent in the presence of a Ni, Co, Fe, As, Mo, O catalyst.

U.S. Pat. No. 3,778,386 describes a vapor phase oxidation process in which propylene can be converted to acrolein in a single pass yield up to 88 percent.

$$\text{Single pass yield} = \frac{\text{moles of acrolein}}{\text{moles of propylene supplied}} \times 100$$

The U.S. Pat. No. 3,778,386 catalyst contained the following elements on a suitable carrier or binder:

$$Ni_aCo_bFe_cBi_dL_eM_hMo_fO_g$$

wherein Ni, Co, Fe, Bi, Mo and O are the elements nickel, cobalt, iron, bismuth, molybdenum and oxygen, respectively; L is phosphorous, arsenic or boron, including mixtures; and M is potassium, rubidium or cesium, including mixtures; and wherein a and b are 0 to 15, while a plus b is 2 to 15, c is 0.5 to 7, d is 0.1 to 4, e is 0 to 4, f is 12, g is 35 to 85 and h is 0.01 to 0.5

U.S. Pat. No. 4,001,317 describes a process for the preparation of unsaturated aldehydes and acids from propylene or isobutylene by the vapor phase oxidation of propylene or isobutylene with molecular oxygen at a temperature of about 200° to 600° C. in the presence of a catalyst, the improvement comprising using as the catalyst a catalyst of the formula:

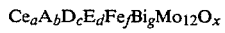

$$Ce_aA_bD_cE_dFe_fBi_gMo_{12}O_x$$

wherein A is an alkali metal, Tl or a mixture thereof; D is Ni, Co, Mg, Zn, Cd, Ca, Sr or mixture thereof; E is P, As, B, S, Al or mixture thereof; and wherein a is greater than 0 but less than 5; b and d are 0–4; c, f and g are 0.1–12; and x is the number of oxygens required to satisfy the valence requirements of the other elements present.

As noted in the above described prior art processes, when propylene or isobutylene is catalytically oxidized into acrolein or methacrolein in the vapor phase, substantial amounts of byproducts are formed such as carbon monoxide, carbon dioxide, saturated aldehydes (e.g., formaldehyde and acetaldehyde) and acids (e.g., acetic acid and acrylic acid). Furthermore, catalysts which promote acceptable conversion yield and selectivity in the vapor phase oxidation of propylene or isobutylene to acrolein or methacrolein often exhibit a short catalyst life.

Accordingly, it is a main object of this invention to provide an improved process for high single pass conversion of olefins into the corresponding unsaturated aldehyde derivatives.

It is another object of this invention to provide an improved oxidation catalyst for conversion of acrolein or isobutylene to acrolein or methacrolein with a single pass olefin conversion of at least 95 percent and an unsaturated aldehyde product efficiency of at least 70 percent.

It is a further object of this invention to provide a process for preparing a Mo-Co-Fe-Ni-Bi-K-P-O oxidation catalyst which exhibits extended catalytic activity in vapor phase olefin oxidation processes.

Other objects and advantages shall become apparent from the accompanying description and examples.

DESCRIPTION OF THE INVENTION

One or more objects of the present invention are accomplished by the provision of a process for preparing an oxidation catalyst corresponding to the formula:

$$Mo_{12}Co_{1.7}Fe_{1.6}Ni_{1.6}Bi_{0.3-3}L_{0.55-2}M_{0.3-0.6}O_x$$

wherein Mo, Co, Fe, Ni, Bi and O are respectively the elements of molybdenum, cobalt, iron, nickel, bismuth and oxygen; L is at least one element selected from potassium and rubidium; M is at least one element selected from phosphorus, cerium, germanium, manganese, niobium, antimony and tantalum; and x represents the number of oxygen atoms between about 35 and 75 sufficient to satisfy the valence requirements of the other elements; said process comprising the steps of (1) admixing and slurrying in an aqueous medium respectively compounds of Mo, Co, Fe, Ni, Bi, L and M which are at least partially water-soluble, (2) adjusting the final pH of the aqueous slurry admixture within the range between about 1–5, (3) concentrating the aqueous slurry admixture by water removal to yield a catalyst coprecipitate, (4) heating the catalyst coprecipitate at a temperature in the range between about 200°–250° C. in the presence of molecular oxygen, and (5) calcining the catalyst composition at a temperature between about 400°–600° C. in the presence of molecular oxygen.

More particularly, it has been found that exceptional catalytic reactivity and selectivity for vapor phase oxidation of olefinically unsaturated hydrocarbons to the corresponding olefinically unsaturated aldehydes is achieved with a preferred type of catalyst composition which corresponds to the formula:

$$Mo_{12}Co_{4.5}Fe_{2.4}Ni_{2.3}Bi_{0.5-2}K_{0.6-1.4}P_{0.35-0.5}O_x$$

Important advantages are achieved in the practice of the present invention when in accordance with the above formula specific relative proportions of potassium and phosphorus are incorporated in the oxidation catalyst composition. In vapor phase olefin oxidation processes, the said preferred type of oxidation catalyst exhibits a high level of activity without a concomitant increase in reaction exotherm which is difficult to control.

The preferred type of invention oxidation catalyst is exceptionally effective for close to 100 percent conversion of olefins such as propylene and isobutylene to oxidation products. Further, the said preferred type of present invention oxidation catalyst is highly selective in the conversion of olefins such as propylene and isobutylene to the corresponding aldehydes such as acrolein and methacrolein. Also to be noted as a particularly important characteristic of the preferred oxidation catalyst composition is the ability to catalyze a vapor phase olefin oxidation reaction over an extended catalyst lifetime essentially without loss of catalytic reactivity and selectivity.

CATALYST PREPARATION

As stated hereinabove, the oxidation catalyst of the present invention has a superior combination of properties which is achieved by a novel method of preparation, which method involves the physical and chemical interaction of specific components in narrowly specific proportions to yield a complex chemical composition of unique structure.

In the invention method of catalyst preparations, compounds of Mo, Co, Ni, Bi, L and M are admixed and slurried in an aqueous medium. Normally it is preferred to incorporate in successive order compounds which are water-soluble or at least partially water-soluble to facilitate formation of the ultimate catalyst crystalline structure. In a typical preparation, dilute phosphoric acid is added to an aqueous solution of a molybdate compound such as ammonium molybdate. If the physical properties of the particular catalyst are to be enhanced by the addition of a binder material such as Cab-O-Sil, aerosil or silica sol, at this point in the procedure an appropriate amount is stirred into the aqueous medium.

Then the calculated quantities of compounds of cobalt, nickel, iron and bismuth are successively added to the catalyst preparation medium, preferably in the form of nitrate salts. The addition is facilitated if each of the nitrate compounds is pre-dissolved in water before the successive addition to the catalyst preparation medium. It is advantageous to pre-dissolve the bismuth salt in dilute nitric acid solution before it is added to the preparation medium. It is to be noted that in the herein described catalyst component addition procedure, the formation of an insoluble precipitate is usually observed upon the addition of the iron nitrate to the catalyst preparation medium.

The successive addition of catalyst components is continued with the addition of a water-soluble compound of potassium such as potassium nitrate or potassium hydroxide. As illustrated in Examples VI, IX and XIII, it is to be noted that the potassium component also can be added in the early stage of the catalyst preparation sequence along with the phosphorus (or equivalent) component.

After the completion of the successive addition of catalyst components, it is essential that the pH of the resultant catalyst preparation medium is in the range between about 1–5, and preferably in the range between about 1.8–3.6. The pH of the catalyst preparation medium can be adjusted by the addition of an acid or base as required, such as by the addition of nitric acid or ammonium hydroxide.

The resultant catalyst preparation medium is concentrated to dryness, such as by spray-drying or by means of a roto-vacuum apparatus. The catalyst precursor solids are recovered and then subjected to a heat treatment at a temperature in the range between about 200°–250° C. in contact with air to effect precalcination of the catalyst precursor mass. The period of heat treatment on the average will be in the range between about 1–24 hours.

The final form of the invention catalyst composition is obtained by calcining the catalyst precursor mixture at a temperature in the range between about 400°–600° C. in the presence of molecular oxygen. The calcination procedure preferably is conducted for a period of time sufficient for the catalyst composition to stabilize in its highest oxidation state, e.g., a calcination period between about 4–20 hours at a temperature in the range of about 450°–550° C.

The activity of these catalysts is a complex function of calcination procedure, final slurry pH, and potassium level. Calcination at the lower end of the temperature range results in a more active catalyst such as would be more suitable for use with propylene, while calcination at the higher end results in a less active catalyst more suitable for use with isobutylene. Increasing potassium decreases the activity. A final slurry pH in the low end of the desired range will result in a catalyst that is more active than one prepared from a final slurry with a pH mid-range or above.

It is believed that the present invention oxidation catalyst has a complex molybdate phase containing Ni, Fe, K, and P in which are embedded very small crystallites of various phases of $Bi_2O_3$, $Bi_2MoO_6$, $Bi_{20}MoO_{33}$ and $CoMoO_4$. Catalysts outside the present invention that contained excessively high levels of K or those with K replaced by Mg, Ba, or Cs for instance did not tend to contain identifiable crystallites of these Bi containing phases but often gave indications of $Bi_2Mo_3O_{11}$ instead.

The complex molybdate phase (or phases) is sufficiently disordered to give a very poor PXRD pattern which appears to be similar to the various modifications of $CoMoO_4$.

Catalysts with compositions within the desired range but prepared with a final slurry pH outside the present invention exhibit a PXRD pattern different from catalysts prepared with both proper composition and proper final slurry pH. The most easily noted difference is an excessively high level of $MoO_3$ for those catalysts outside the pH range on the low side. Those outside the pH range on the high side show a great increase in intensity of the strongest $CoMoO_4$ associated reflection and a slight shifting of this line to higher $2\theta$ values. The Fourier Transform Infrared spectrum of these catalysts also show significant changes in the molybdate region over those with a proper final slurry pH. It is believed these changes are associated with changes in the complex molybdate phase (or phases) containing Fe, Ni, K and P mentioned earlier.

The physical form of the final catalyst composition can be varied as desired as rough granules, as pellets, extrudate, or coated on the surface of suitable inert spheres or spheroids. These spheres or spheroids most suitably have a rough surface texture and are of silicon carbide, silica, and the like.

OXIDATION OF OLEFINS

One or more further objects and advantages of the present invention are accomplished by the provision of a process for the oxidation of olefinically unsaturated hydrocarbons to the corresponding olefinically unsaturated aldehydes which comprises reacting in the vapor phase an olefinically unsaturated hydrocarbon with molecular oxygen in the presence of an oxidation catalyst which corresponds to the formula:

$$Mo_{12}Co_{1-7}Fe_{1-6}Ni_{1-6}Bi_{0.3-3}L_{0.55-2}M_{0.3-0.6}O_x$$

wherein Mo, Co, Fe, Ni, Bi and O are respectively the elements of molybdenum, cobalt, iron, nickel, bismuth and oxygen; L is at least one element selected from potassium and rubidium; M is at least one element selected from phosphorus, cerium, germanium, manganese, niobium, antimony and tantalum; and x represents the number of oxygen atoms between about 35 and 75 sufficient to satisfy the valence requirements of the other elements.

In another preferred embodiment, the present invention provides a process wherein said molecular oxygen is contained in an air stream diluted with a gas selected from steam, nitrogen and carbon dioxide.

The term "olefinically unsaturated hydrocarbons" as employed herein is meant to include alkenes containing between 3 and about 5 carbon atoms as a preferred class of starting materials. It is understood that organic derivatives such as tertiary-butanol or alkyl tertiary-butyl ether (e.g., $C_1$–$C_4$ alkyl such as methyl) may be employed in the vapor phase oxidation process, which derivatives convert to olefinically unsaturated hydrocarbons (e.g., isobutylene) in situ during the oxidation process.

The oxidation process of the present invention utilizing the novel catalysts may be carried out continuously or noncontinuously and the catalyst may be present in various forms such as in fixed beds or as a fluidized system. Portions of the reactants which do not undergo reaction may be recycled if desired.

The temperatures utilized should generally range between about 200° to 525° C., although the exact temperature utilized in a particular situation will depend largely on the desired product distribution. Thus if it is desired to produce an oxygenated product consisting largely of unsaturated aldehyde with little or no formation of unsaturated acid, then temperatures in the range between about 300° to 400° C. are preferred. However if it is desired to produce a product which contains a minor portion of unsaturated acid in addition to the major portions of unsaturated aldehyde, then higher temperatures in the range of 400° to 525° C. are preferably utilized. The production of mixtures of unsaturated aldehydes and acids are generally most advantageous when the product is to be further oxidized in a second step so as to produce unsaturated acids as the ultimate end product. For example, a two-step process may be utilized for converting propylene to acrylic acid.

The pressure utilized in the process of the present invention may be subatmospheric, atmospheric or superatmospheric but should be between about 0.5 to 3.0 atmospheres for best results, although pressures ranging up to 10 atmospheres may be suitably employed. The contact time for the reactants with the catalyst under the reaction conditions should generally range between about 0.1 to 40 seconds but is preferably a time within the range between about 0.5 to 5 seconds. It has been found that in addition to being dependent on the temperature, the amount of unsaturated acid produced at a given termperature and pressure will increase as the contact time increases. Thus, where it is desired to produce little or no amount of unsaturated acid, the contact time will generally be between 0.1 to 10 seconds, and will usually be between about 4 to 15 seconds when it is desired to produce a product containing a minor portion of unsaturated acid in addition to the unsaturated aldehyde. As used herein the term "contact time" refers to the contact time adjusted to 25° C. and atmospheric pressure. The contact time is calculated by dividing the volume of the catalyst bed (including voids) by the volume per unit time flow rate of the reactants at NTP.

The oxygen source necessary as a reactant in the process may be from concentrated molecular oxygen or may be from a more dilute oxygen-containing gas wherein the molecular oxygen is mixed in varying amounts with an inert diluent gas such as nitrogen, argon or carbon oxides. Preferably, air is utilized as the source of oxygen. The olefinically unsaturated hydrocarbon and/or oxygen-containing gas may be separately introduced into the reaction zone at one or a plurality of points along the length of the reaction zone or may be premixed before entering the reaction zone. However the contact of the olefin and the oxygen-containing charge are preferably kept to a minimum before entering the reaction zone such as for the removal of undesirable components therefrom.

In conducting the oxidation reaction, the gaseous feed mixture should generally contain about 1.0 to 7.0 moles of oxygen per mole of the olefinically unsaturated hydrocarbon, although the preferred range is between about 2.0 and 5.0 moles per mole. Although it is not required, water in the form of steam is also desirably present in the gaseous feed in amounts of from 0.5 to 15, preferably 2.0 to 15, moles per mole of unsaturated hydrocarbon. In addition to steam, diluents which are gaseous under the reaction conditions and are relatively inert may be introduced into the system. Suitable diluents include carbon dioxide, nitrogen and flue gas, as well as paraffinic hydrocarbons such as are frequently present in commercially-available propylene and isobutylene (e.g., mixtures of propane and propylene obtained from cracking units).

In accordance with the present invention process for oxidizing propylene or isobutylene to acrolein or methacrolein, a single pass conversion of 95 percent of the olefinically unsaturated hydrocarbon feed stream is readily achieved. Further, a single pass conversion efficiency (i.e., selectivity) of propylene and isobutylene to acrolein or methacrolein is at least 70 percent under the preferred vapor phase processing conditions described above. Also of importance for the purposes of a two-step commercial operation, in which the present invention process represents the first stage, is the ability of the said invention process to provide a single pass yield of acrolein/acrylic acid or methacrolein/methacrylic acid of at least 70 percent at a space time yield (STY) of at least 225 grams per liter per hour.

The following examples are further illustrative of the present invention. The reactants and other specific ingredients are presented as being typical, and various modifications can be devised in view of the foregoing disclosure within the scope of the invention.

EXAMPLE I

Preparation Of
$Mo_{12}Co_{4.5}Fe_3Ni_{2.5}Bi_1K_{0.7}P_{0.425}O_x/SiO_2$ As A Selective Oxidation Catalyst An 88.3 gram quantity of $(NH_4)_6Mo_7O_{24}.4H_2O$ was disolved in 200 milliliters of doubly distilled water, and to the solution 2.04 grams of $(NH_4)H_2PO_4$ were added. The pH of the resultant blend was 5.6. As a next step 55.4 grams of Nalco 40% SiO$_2$, type 2327 SiO$_2$ (particle size 20 m$\mu$, 150 M$^2$/gm less than 0.1% Na$_2$O). To this slurry a solution of 54.6 grams of Co(NO$_3$)$_2$.6H$_2$O and 30.3 grams of Ni(NO$_3$)$_2$.6H$_2$O in 200 milliliters of doubly distilled water was added. The resulting combined slurry had a pH of 2-2.5.

To this slurry a solution of 50.5 grams of Fe(NO$_3$)$_3$.9-H$_2$O in 100 milliliters of doubly distilled water was added. The resultant thick yellow slurry had a pH of about 1. Then 20.21 grams of Bi(NO$_3$)$_3$.5H$_2$O dissolved in 40 milliliters of 10% HNO$_3$ was added followed by 3.0 grams of KNO$_3$ in 25 milliliters of doubly distilled water. While the resulting slurry was being rapidly stirred, the pH was adjusted with a 20% solution of NH$_4$OH to 3-3.5 (the slurry color changed from bright yellow to tan yellow).

The slurry was subjected to 5 minutes of efficient blending, and then concentrated in a rotary evaporator for 16 hours at 120° C. under 0.5 atmospheric pressure. The coprecipitate mixture of catalyst precursor solids was precalcined at 225° C. for 2 hours, and then calcined at 540° C. for 4 hours. The resulting catalyst composition was crushed and sieved to yield 20-30 mesh catalyst particles.

About 6 cm$^3$ of the catalyst composition were blended with 9 cm$^3$ of 20-30 mesh crushed fused quartz and charged into a 0.337 I.D. reactor tube. A gaseous blend of isobutylene, steam and air was passed through the reactor tube under the processing conditions indicated below.

It has been observed that the properties of the final catalyst composition are affected by the particular sequence of the successive additive of catalyst components to the catalyst preparation medium.

The most preferred catalyst preparation sequence appears to be in the order of (1) the combination of molybdenum compound with phosphorus compound (or equivalent element), and optionally, some or all of the potassium compound; (2) the addition of binder substrate material; (3) the addition of cobalt and nickel compounds; (4) the addition of iron compound, then bismuth compound; and (5) which is followed by the addition of potassium compound (or equivalent element) if not previously incorporated, and the adjustment of pH into the 1-5 range.

In the case where the M element of the catalyst is phosphorus, it is essential that the pH be maintained strictly within the pH range of 1-5. In the case where the M element is germanium or other equivalent of phosphorus, then a somewhat broader pH range of between about 1-6 is permissible during catalyst preparation without any serious deleterious effect on the ultimate oxidation selectivity properties of the catalyst composition.

As an alternative catalyst preparation sequence of component addition, a solution containing cobalt, nickel, iron, bismuth and potassium (or equivalent element) compounds can be added to a solution containing molybdenum and phosphorus (or equivalent element). For reasons that are not readily apparent, a catalyst with a less desirable combination of properties is obtained if the solution of molybdenum and phosphorus compounds is added to the solution of cobalt, nickel, iron, bismuth and potassium compounds, rather than vice versa.

TABLE I

| 40% (84% Mo$_{12}$Co$_{4.5}$Fe$_3$M$_{2.5}$Bi$_1$K$_{0.7}$P$_{0.425}$O$_x$/16% SiO$_2$) + 60% SiO$_2$ | | | | | | | |
|---|---|---|---|---|---|---|---|
| Feed, | mole % | Temp. °C. | | Contact Time | iC$_4$= Conv. | MA$^{(1)}$ Eff. | MA + MAA$^{(2)}$ |
| iC$_4$= | Steam | Bath | Peak | Sec. | % | % | Yld % | STY g/l-hr |
| 3.0 | 37.0 | 382 | 435 | .75 | 98.1 | 72.9 | 72.2 | 358 |
| 3.0 | 37.0 | 383 | 435 | .75 | 98.2 | 73.9 | 73.6 | 358 |
| 3.0 | 37.0 | 383 | 435 | .75 | 98.0 | 72.9 | 72.6 | 368 |

$^{(1)}$methacrolein
$^{(2)}$methacrylic acid

EXAMPLE II

Preparation Of Mo$_{12}$Co$_{4.5}$Fe$_3$Ni$_{2.5}$Bi$_1$K$_{0.7}$P$_{0.25}$O$_x$ Oxidation Catalyst The procedure of Example I was followed, with the exception that a smaller quantity of phosphorus-containing compound was employed, and silicon carbide was incorporated as the inert diluent.

The phosphorus content of this catalyst was outside of the range of the present invention catalyst definition (i.e., P$_{0.3-0.6}$). Less desirable results were obtained when this catalyst was utilized for conversion of isobutylene to methacrolein/methacrylic acid.

TABLE II

| 40% (84% Mo$_{12}$Co$_{4.5}$Fe$_3$Ni$_{2.5}$Bi$_1$K$_{0.7}$P$_{0.25}$O$_x$/16% SiO$_2$) + 60% SiC | | | | | | | |
|---|---|---|---|---|---|---|---|
| Feed, | mole % | Temp. °C. | | Contact Time | iC$_4$= Conv. | MA Eff. | MA + MAA |
| iC$_4$= | Steam | Bath | Peak | Sec. | % | % | Yld % | STY g/l-hr |
| 3.0 | 38.1 | 345 | 393 | .8 | 93 | 67 | 64 | 316 |

EXAMPLE III

Preparation of Mo$_{12}$Co$_{4.5}$Fe$_3$Ni$_{2.5}$Bi$_1$K$_{1.4}$P$_{0.9}$O$_x$ Oxidation Catalyst The procedure of Example I was followed, with the exception that a greater quantity of phosphorus-containing compound was employed.

The phosphorus content of this catalyst was outside of the present invention catalyst definition (i.e., P$_{0.3-0.6}$). Less desirable results were obtained when this catalyst was utilized for the conversion of isobutylene to methacrolein/methacrylic acid.

TABLE III

| | | | | | | | | |
|---|---|---|---|---|---|---|---|---|
| 40% (84% % $Mo_{12}Co_{4.5}Fe_3Ni_{2.5}Bi_1K_{1.4}P_{0.9}O_x$/16% $SiO_2$) + 60% $SiO_2$ | | | | | | | | |
| Feed, | mole % | Temp. °C. | | Contact Time | $iC_4=$ Conv. | MA Eff. | MA + MAA | |
| $iC_4=$ | Steam | Bath | Peak | Sec. | % | % | Yld % | STY g/l-hr |
| 4.3 | 34.9 | 372 | 392 | 1.7 | 96 | 65 | 64 | 205 |
| 4.3 | 34.9 | 366 | 376 | 1.8 | 90 | 69 | 63 | 220 |
| 4.4 | 34.9 | 367 | 384 | 1.7 | 90 | 66 | 61 | 217 |

EXAMPLE IV

Preparation Of $Mo_{12}Co_{4.5}Fe_3Ni_{2.5}Bi_1K_{1.75}P_{0.9}O_x$ Oxidation Catalyst The catalyst was prepared in the manner of Example I, with the exception that larger quantities of potassium and phosphorus source compounds were employed.

The potassium content of this catalyst was toward the upper limit of the present invention catalyst definition (i.e., $K_{0.5-2}$), and the phosphorus content was outside of the present invention catalyst definition ($P_{0.3-0.6}$). Relatively poor results were obtained when this catalyst not in accordance with the present invention was utilized for the conversion of isobutylene to methacrolein/methacrylic acid.

TABLE IV

| | | | | | | | | |
|---|---|---|---|---|---|---|---|---|
| 40% (84% $Mo_{12}Co_{4.5}Fe_3Ni_{2.5}Bi_1K_{1.75}P_{0.9}O_x$/16% $SiO_2$) + 60% $SiO_2$ | | | | | | | | |
| Feed, | mole % | Temp. °C. | | Contact Time | $iC_4=$ Conv. | MA Eff. | MA + MAA | |
| $iC_4=$ | Steam | Bath | Peak | Sec. | % | % | Yld % | STY g/l-hr |
| 4.3 | 34.5 | 420 | 434 | 1.6 | 82 | 59 | 49 | 168 |
| 4.3 | 34.5 | 425 | 440 | 1.6 | 82 | 58 | 49 | 168 |

EXAMPLE V

Preparation of $Mo_{12}Co_{4.5}Fe_3Ni_{2.5}Bi_1K_{0.8}P_{0.4}O_x$ Oxidation Catalyst In a manner similar to Example I, 79.2 grams $(NH_4)_6Mo_7O_{24}.4H_2O$ and 1.75 grams of 86.1% $H_3PO_4$ were dissolved in 200 milliliters of water, to which 56 grams Nalco 40% $SiO_2$ (type 2327) were added. This was followed by the following addition sequence:

(a) 49.0 grams of $Co(NO_3)_2.6H_2O$ and 27.2 grams of $Ni(NO_3)_2.6H_2O$ in 100 milliliters of water.

(b) 45.3 grams of $Fe(NO_3)_3.9H_2O$ and 3.02 grams of $KNO_3$ in 100 milliliters of water.

(c) 18.1 grams of $Bi(NO_3)_3.5H_2O$ in 20 milliliters of water and 2 milliliters of conc. $HNO_3$.

The pH of the final slurry was <1. The recovery of catalyst precursor solids, and the subsequent calcination and grinding to yield the final catalyst composition were in accordance with the Example I procedure.

Because the final pH of the catalyst preparation medium was less than 1, the properties of the ultimate catalyst composition were adversely affected, and less desirable results were obtained when this catalyst was utilized for conversion of isobutylene to methacrolein/methacrylic acid.

TABLE V

| | | | | | | | | |
|---|---|---|---|---|---|---|---|---|
| 40% (84% $Mo_{12}Co_{4.5}Fe_3Ni_{2.5}Bi_1K_{0.8}P_{0.4}O_x$/16% $SiO_2$) + 60% $SiO_2$ | | | | | | | | |
| Feed, | mole % | Temp. °C. | | Contact Time | $iC_4=$ Conv. | MA Eff. | MA + MAA | |
| $iC_4=$ | Steam | Bath | Peak | Sec. | % | % | Yld % | STY g/l-hr |
| 3.0 | 36.9 | 337 | 378 | 1.2 | 98 | 62 | 62 | 207 |
| 3.0 | 36.9 | 340 | 388 | 1.2 | 99 | 59 | 60 | 213 |

EXAMPLE VI

Preparation of $Mo_{12}Co_{4.5}Fe_3Ni_{2.5}Bi_1K_{0.7}Mn_{0.4}O_x$ Oxidation Catalyst In the manner of Example I, 79.2 grams $(NH_4)_6Mo_7O_{24}.4H_2O$ were dissolved in 200 milliliters of water. To the solution were added 2.36 grams of $KMnO_4$ dissolved in 50 milliliters of water, followed by 49.0 grams $Co(NO_3)_2.6H_2O$ and 27.2 grams of $Ni(NO_3)_2.6H_2O$ dissolved in 200 milliliters of water, and 45.3 grams $Fe(NO_3)_3.9H_2O$ in 50 milliliters of water followed by 18.1 grams of $Bi(NO_3)_3.5H_2O$ in 30 milliliters of 10% $HNO_3$, 1.13 grams of $KNO_3$ in 25 milliliters of water, and then 55 grams of Nalco 40% $SiO_2$ (type 2327). After 2.5 minutes of efficient blending, the final pH was adjusted to 3 with $NH_4OH$.

After the drying, denitrification and calcination operations were completed, the catalyst was utilized for the oxidation of isobutylene as summarized in the Table.

TABLE VI

| | | | | | | | | |
|---|---|---|---|---|---|---|---|---|
| 40% (84% $Mo_{12}Co_{4.5}Fe_3Ni_{2.5}Bi_1K_{0.7}Mn_{0.4}O_x$/16% $SiO_2$) + 60% $SiO_2$ | | | | | | | | |
| Feed, | mole % | Temp. °C. | | Contact Time | $iC_4=$ Conv. | MA Eff. | MA + MAA | |
| $iC_4=$ | Steam | Bath | Peak | Sec | % | % | Yld % | STY g/l-hr |
| 3.5 | 37.1 | 354 | 409 | .78 | 96 | 70 | | 69 |

EXAMPLE VII

Preparation of $Mo_{12}Co_{4.5}Fe_3Ni_{2.5}Bi_1K_{0.7}Nb_{0.5}O_x$ Oxidation Catalyst In the manner of Example I, 79.2 grams of $(NH_4)_6Mo_7O_{24}\cdot 4H_2O$ was dissolved in 200 milliliters of water, and 50 milliliters of 29% $NH_3$ solution. To this mixture was added 55 grams of Nalco 40% $SiO_2$ (type 2327) and 1.99 grams of $Nb_2O_5$. Standard solutions of Co and Ni, Fe, Bi and K compound were added in sequence and then the final slurry pH was adjusted to 3.0–3.5 with $NH_3$ solution. Example I drying, denitrification and calcination operations were employed to produce the catalyst compositions in final form.

The catalyst was utilized for isobutylene oxidation with the results listed below.

TABLE VII

| 40% (84% $Mo_{12}Co_{4.5}Fe_3Ni_{2.5}Bi_1K_{0.7}Nb_{0.5}O_x$/16% $SiO_2$) + 60% $SiO_2$ | | | | | | | | |
|---|---|---|---|---|---|---|---|---|
| Feed, | mole % | Temp. °C. | | Contact Time | $iC_4=$ Conv. | MA Eff. | MA + MAA Yld | STY |
| $iC_4=$ | Steam | Bath | Peak | Sec. | % | % | % | g/l-hr |
| 2.9 | 36.9 | 364 | 395 | .80 | 98 | 70 | 70 | 386 |
| 2.9 | 37.1 | 365 | 395 | .80 | 98 | 71 | 69 | 388 |
| 2.9 | 37.7 | 361 | 393 | .81 | 98 | 70 | 70 | 360 |
| 2.9 | 37.7 | 362 | 391 | .82 | 97 | 70 | 70 | 352 |
| 2.9 | 37.7 | 361 | 392 | .82 | 97 | 71 | 70 | 365 |
| 2.9 | 37.7 | 361 | 391 | .82 | 97 | 72 | 71 | 379 |

EXAMPLE VIII

Preparation of $Mo_{12}Co_{4.5}Fe_3Ni_{2.5}Bi_1K_{0.7}Ce_{0.5}O_x$ Oxidation Catalyst As in Example I, to 79.2 grams $(NH_4)_6Mo_7O_{24}\cdot 4H_2O$ in 150 milliliters of water and 150 milliliters 29% $NH_3$ solution were added 10.25 grams $(NH_4)_2Ce(NO_3)_6$ in 50 milliliters of water. A cream yellow suspension resulted, to which was added 55 grams of Nalco 40% $SiO_2$ (type 2327). As a next step there was added 49.0 grams $Co(NO_3)_2\cdot 6H_2O$ and 27.2 grams $Ni(NO_3)_2\cdot 6H_2O$ in 200 milliliters of water. The resultant lavender colored suspension had a pH of 8.0. To this suspension was added 45.2 grams $Fe(NO_3)_3\cdot 9H_2O$ in 100 milliliters of water. The suspension turned salmon-pink and then orange brown. The measured pH of the suspension was 6.0. Next were added 18.1 grams of $Bi(NO_3)_3\cdot 5H_2O$ and 2.64 grams of $KNO_3$ in 30 milliliters of 10% $HNO_3$. The final pH was adjusted to 5.0–5.5, and Example I blending, drying, precalcining and calcining procedures were followed. The catalyst was evaluated for isobutylene oxidation reactivity.

TABLE VIII

| 40% (84% $Mo_{12}Co_{4.5}Fe_3Ni_{2.5}Bi_1K_{0.7}Ce_{0.5}O_x$/16% $SiO_2$) + 60% $SiO_2$ | | | | | | | | |
|---|---|---|---|---|---|---|---|---|
| Feed, | mole % | Temp. °C. | | Contact Time | $iC_4=$ Conv. | MA Eff. | MA + MAA Yld | STY |
| $iC_4=$ | Steam | Bath | Peak | Sec. | % | % | % | g/l-hr |
| 3.0 | 36.3 | 343 | 373 | 1.2 | 97 | 70 | 70 | 230 |
| 3.0 | 36.5 | 343 | 373 | 1.2 | 98 | 69 | 69 | 232 |
| 2.9 | 37.3 | 345 | 385 | .82 | 97 | 72 | 71 | 343 |
| 2.9 | 37.3 | 345 | 384 | .82 | 96 | 73 | 71 | 338 |
| 2.9 | 37.2 | 347 | 390 | .81 | 98 | 71 | 71 | 344 |
| 2.9 | 36.9 | 347 | 393 | .81 | 98 | 70 | 70 | 349 |

EXAMPLE IX

Preparation of $Mo_{12}Co_{4.5}Fe_3Ni_{2.5}Bi_1K_{0.7}Ge_{0.5}O_x$ Oxidation Catalyst A 1.95 gram quantity of $GeO_2$ was partially dissolved in 100 milliliters of water containing 1.8 grams of 86.1% KOH. This preparation was added to 200 milliliters of solution containing 79.2 grams of $(NH_4)_6Mo_7O_{24}\cdot 4H_2O$. A clear yellow solution of pH 6.0 resulted. To the solution was added 49.0 grams of $Co(NO_3)_2\cdot 6H_2O$ and 27.2 grams of $Ni(NO_3)_2\cdot 6H_2O$ in 100 milliliters of water. The clear dark solution developed a precipitate after five minutes. To this slurry was added 45.3 grams of $Fe(NO_3)_3\cdot 9H_2O$ in 50 milliliters of water. A copious quantity of a yellow precipitate resulted. Sufficient $NH_4OH_x$ was added to raise the pH to 4.5. Then 18.1 grams of $Bi(NO_3)_3\cdot 5H_2O$ in 30 milliliters of 10% $HNO_3$ and 55 grams of Nalco 40% $SiO_2$ (type 2327) were added. The final pH was 3.5 Example I blending, drying, precalcination and calcination procedures were followed to yield a final catalyst composition which was evaluated for isobutylene oxidation reactivity.

TABLE IX

| 40% (84% $Mo_{12}Co_{4.5}Fe_3Ni_{2.5}Bi_1K_{0.7}Ge_{0.5}O_x$/16% $SiO_2$) + 60% $SiO_2$ | | | | | | | | |
|---|---|---|---|---|---|---|---|---|
| Feed, | mole % | Temp. °C. | | Contact Time | $iC_4=$ Conv. | MA Eff. | MA + MAA Yld | STY |
| $iC_4=$ | Steam | Bath | Peak | Sec. | % | % | % | g/l-hr |
| 3.1 | 36.7 | 356 | 399 | 1.2 | 99 | 68 | 69 | 273 |
| 2.9 | 37.4 | 363 | 401 | .80 | 97 | 72 | 71 | 361 |

EXAMPLE X

Preparation of $Mo_{12}Co_{4.5}Fe_3Ni_{2.5}Bi_1K_{0.7}Zr_{0.45}O_x$ Catalyst for Comparison of Oxidation Properties The catalyst preparation procedures of Example I were employed, except that there was substituted 8.46 grams of $ZrO(NO_3)_2$ in 40 milliliters of 30% $HNO_3$ in combination with 79.2 grams of $(NH_4)_6Mo_7O_{24}\cdot 4H_2O$ in 200 milliliters of water, thereby replacing phosphorus content with zirconium content.

TABLE XI

40% (84% $Mo_{12}Co_{4.5}Fe_3Ni_{2.5}Bi_1K_{0.7}Ce_{0.2}Nb_{0.2}O_x$/16% $SiO_2$) + 60% $SiO_2$

| Feed, mole % | | Temp. °C. | | Contact Time | $iC_4=$ Conv. | MA Eff. | MA + MAA | |
|---|---|---|---|---|---|---|---|---|
| $iC_4=$ | Steam | Bath | Peak | Sec. | % | % | Yld % | STY g/l-hr |
| 2.9 | 36.4 | 352 | 408 | 1.17 | 94.7 | 71.3 | 67.8 | 238 |
| 2.9 | 36.7 | 363 | 440 | .73 | 96.8 | 69.8 | 68.2 | 378 |

This catalyst composition was not within the scope of the present invention catalyst definition. The catalyst exhibited poor selectivity when tested for the oxidation of isobutylene to methacrolein.

TABLE X

40% (84% $Mo_{12}Co_{4.5}Fe_3Ni_{2.5}Bi_1K_{0.7}Zr_{0.45}O_x$/16% $SiO_2$) + 60% $SiO_2$

| Feed, mole % | | Temp. °C. | | Contact Time | $iC_4=$ Conv. | MA Eff. | MA+MAA | |
|---|---|---|---|---|---|---|---|---|
| $iC_4=$ | Steam | Bath | Peak | Sec. | % | % | Yld % | STY g/l-hr |
| 3.1 | 37.5 | 416 | 449 | 1.12 | 97.3 | 30 | — | — |

EXAMPLE XI

Preparation of $Mo_{12}Co_{4.5}Fe_3Ni_{2.5}Bi_1K_{0.7}Ce_{0.2}Nb_{0.2}O_x$ Oxidation Catalyst To 79.2 grams of $(NH_4)_6Mo_7O_{24}.4H_2O$ in 200 milliliters of water were added 4.1 grams of ceric ammonium nitrate in 50 milliliters of water, followed by addition of 1.0 gram of $Nb_2O_5$ which was dispersed in 25 milliliters of water. As a next step 55 grams of Nalco 40% $SiO_2$ (type 2327) was added. The pH of the mixture was 6.

Then 49.0 grams of $Co(NO_3)_2.6H_2O$ and 27.2 grams of $Ni(NO_3)_2.6H_2O$ were dissolved in 200 milliliters of water and added to the above mixture. The brown slurry which resulted had a pH of 6. A 45.2 gram quantity of $Fe(NO_3)_3.9H_2O$ in 100 milliliters of water was added to the above described mixture, and the resultant orange-brown slurry had a pH of 0.5.

Subsequently, a solution of 18.1 grams of $Bi(NO_3)_3.5H_2O$ dissolved in 30 milliliters of 10% $HNO_3$ was added, followed by addition of 2.64 grams of $KNO_3$ dissolved in 20 milliliters of water. $NH_4OH$ was employed to adjust the pH to 3.0 to 3.5, and then the mixture was subjected to 5 minutes of efficient blending before the drying, denitrification and calcination procedures.

EXAMPLE XII

Preparation of $Mo_{12}Co_{4.5}Fe_3Ni_{2.5}Bi_1K_{0.7}Ge_{0.05}P_{0.3}O_x$ Oxidation Catalyst To 79.2 grams of $(NH_4)_6Mo_7O_{24}.4H_2O$ dissolved in 250 milliliters of water was added a mixture consisting of 0.2 gram of $GeO_2$ dispersed in 100 milliliters of solution containing 1.5 grams of $(NH_4)_2HPO_4$. The pale yellow mixture had a pH of 6.0. In a next step 55 grams of Nalco 40% $SiO_2$ (type 2327) were added, followed by standard amounts of Co and Ni, Fe, Bi and K nitrate solutions. The final slurry pH was adjusted to 3.0–3.5 and Example I blending, drying, denitrification, and calcination procedures were followed to produce the final form of the catalyst composition.

TABLE XII

40% (84% $Mo_{12}Co_{4.5}Fe_3Ni_{2.5}Bi_1K_{0.7}Ge_{0.5}P_{0.3}O_x$/16% $SiO_2$) + 60% $SiO_2$

| Feed, mole % | | Temp. °C. | | Contact Time | $iC_4=$ Conv. | MA Eff. | MA + MAA | |
|---|---|---|---|---|---|---|---|---|
| $iC_4=$ | Steam | Bath | Peak | Sec. | % | % | Yld % | STY g/l-hr |
| 3.0 | 39.4 | 377 | 422 | .79 | 97.4 | 72.0 | 70.5 | 337 |
| 3.0 | 39.4 | 385 | 400 | .79 | 97.4 | 70.8 | 71.2 | 384 |

EXAMPLE XIII

Preparation of $Mo_{12}Co_{4.5}Fe_3Ni_{2.5}Bi_1K_{0.7}Ta_{0.5}O_x$ Oxidation Catalyst To 72.2 grams of $(NH_4)_6Mo_7O_{24}.4H_2O$ dissolved in 200 milliliters of water were added 5.01 grams of $KTaO_3$ and 0.50 grams of 86.1% KOH in 100 milliliters of water. Then there was added 49.0 grams of $Co(NO_3)_2.6H_2O$ and 27.2 grams $Ni(NO_3)_2.6H_2O$ in 100 milliliters of water followed by the addition of 45.3 grams of $Fe(NO_3)_3.9H_2O$ in 100 milliliters of water. The pH of the resultant mixture was <1, and a yellow precipitate was evident. $NH_4OH$ solution was employed to adjust the pH to 3.5, then a solution of 18.1 grams of $Bi(NO_3)_3.5H_2O$ in 30 milliliters of 10% $HNO_3$ was added, followed by the addition of 55 grams of Nalco 40% $SiO_2$ (type 2327). The final slurry pH was 3. Example I blending, drying precalcination and calcination procedures were employed to produce the final form of the catalyst.

TABLE XIII

40% (84% $Mo_{12}Co_{4.5}Fe_3Ni_{2.5}Bi_1K_{0.7}Ta_{0.5}O_x$/16% $SiO_2$) + 60% $SiO_2$

| Feed, mole % | | Temp. °C. | | Contact Time | $iC_4=$ Conv. | MA Eff. | MA + MAA | |
|---|---|---|---|---|---|---|---|---|
| $iC_4=$ | Steam | Bath | Peak | Sec. | % | % | Yld % | STY g/l-hr |
| 3.1 | 37.0 | 362 | 412 | 1.15 | 97.5 | 67.3 | 66.4 | 232 |
| 3.1 | 37.0 | 361 | 408 | 1.18 | 96.4 | 66.9 | 66.8 | 249 |

EXAMPLE XIV

This Example is further illustration of the effect of catalyst preparation pH on the ultimate selective oxidation properties of the catalyst.

A. (pH<1)

To 79.2 grams of $(NH_4)_6Mo_7O_{24}.4H_2O$ in 200 milliliters of water were added 1.75 grams of 86% $H_3PO_4$ and 10.94 grams of Aerosil $SiO_2$. The resulting slurry was a pale greenish yellow. Then 49.0 grams of $Co(NO_3)_2.6H_2O$ and 27.2 grams $Ni(NO_3)_2.6H_2O$ dissolved in 100 milliliters of water were added to the above slurry, followed by the addition of 45.2 grams of $Fe(NO_3)_3.9H_2O$ in 50 milliliters of water, 18.1 grams of $Bi(NO_3)_3.5H_2O$ in 20 milliliters of water containing 3 milliliters of conc. $HNO_3$, 2.64 grams of $KNO_3$ in 30 milliliters of water, and 10.9 grams of Aerosil $SiO_2$. The resulting bright yellow slurry had a pH near zero. The mixture was blended with a Polytron mixer, dried in a rotary evaporator at 120° C. and 0.5 atm, precalcined for 18 hours at 250° C. in air, then calcined at 530° C. in air.

TABLE XIVA

| | | | | | | | MA + MAA | |
|---|---|---|---|---|---|---|---|---|
| 40% (84% $Mo_{12}Co_{4.5}Fe_3Ni_{2.5}Bi_1K_{0.7}P_{0.4}O_x$/16% $SiO_2$) + 60% $SiO_2$ | | | | | | | | |
| Feed, | mole % | Temp. °C. | | Contact Time | iC4= Conv. | MA Eff. | Yld | STY |
| iC4= | Steam | Bath | Peak | Sec. | % | % | % | g/l-hr |
| 2.9 | 36.4 | 335 | 372 | 1.3 | 95 | 67 | 65 | 210 |
| 2.9 | 36.3 | 335 | 371 | 1.3 | 95 | 67 | 65 | 214 |
| 2.9 | 36.3 | 335 | 369 | 1.3 | 94 | 66 | 63 | 215 |
| 2.9 | 36.9 | 345 | 383 | .8 | 89 | 67 | 60 | 293 |
| 2.9 | 36.9 | 355 | 393 | .8 | 95 | 66 | 64 | 304 |
| 2.9 | 36.9 | 365 | 409 | .8 | 95 | 65 | 64 | 306 |
| 2.9 | 36.9 | 365 | 406 | .8 | 96 | 66 | 64 | 309 |

B. (pH=4)

In a similar manner, 88.3 grams of $(NH_4)_6Mo_7O_{24}.4H_2O$ in 200 milliliters of water, 1.92 grams of $NH_4H_2PO_4$, 55 grams of Nalco 40% $SiO_2$, and 54.6 grams of $Co(NO_3)_2.6H_2O$ and 30.3 grams of $Ni(NO_3)_2.6H_2O$ in 150 milliliters of water were combined. Then 50.5 grams of $Fe(NO_3)_3.9H_2O$ in 100 milliliters of water were added, followed by the addition of 20.21 grams of $Bi(NO_3)_3.5H_2O$ in 40 milliliters of 10% $HNO_3$ and 3.0 grams of $KNO_3$ in 50 milliliters of water. The pH of the resultant mixture was adjusted to 4 with $NH_4OH$. The above described precalcination and calcination procedures were employed.

TABLE XIVB

| 40% (84% $Mo_{12}Co_{4.5}Fe_3Ni_{2.5}Bi_1K_{0.7}P_{0.4}O_x$/16% $SiO_2$) + 60% $SiO_2$ | | | | | | | | |
|---|---|---|---|---|---|---|---|---|
| Feed, | mole % | Temp. °C. | | Contact Time | iC4= Conv. | MA Eff. | MA + MAA | |
| iC4= | Steam | Bath | Peak | Sec. | % | % | Yld % | STY g/l-hr |
| 2.6 | 38.0 | 376 | 411 | .80 | 95.7 | 73.7 | 71.2 | 324 |
| 2.6 | 38.0 | 386 | 422 | .78 | 97.2 | 72.2 | 70.9 | 324 |
| 2.6 | 38.0 | 387 | 422 | .78 | 97.2 | 71.4 | 70.3 | 317 |
| 2.6 | 38.0 | 387 | 420 | .79 | 96.7 | 71.9 | 70.4 | 318 |

C. (pH=6)

To 79.2 grams of $(NH_4)_6Mo_7O_{24}.4H_2O$ and 2.03 grams $(NH_4)_2HPO_4$ dissolved in 200 milliliters of water was added sufficient $NH_4OH$ to provide a clear solution of pH 8.0. Then there were added a combination of 54.6 grams of Nalco 40% $SiO_2$ (type 2327), 49.0 grams of $Co(NO_3)_2.6H_2O$, 27.2 grams of $Ni(NO_3)_2.6H_2O$, 45.3 grams of $Fe(NO_3)_3.9H_2O$, 2.64 grams of $KNO_3$ in 200 milliliters of water, and 18.1 grams of $Bi(NO_3)_3.5H_2O$ in 30 milliliters of 10% $HNO_3$. The final pH of the mixture was 6.0. The previously described precalcination and calcination procedures were employed.

TABLE XIVC

| 40% (84% $Mo_{12}Co_{4.5}Fe_3Ni_{2.5}Bi_1K_{0.7}P_{0.4}O_x$/16% $SiO_2$) + 60% $SiO_2$ | | | | | | | | |
|---|---|---|---|---|---|---|---|---|
| Feed, | mole % | Temp. °C. | | Contact Time | iC4= Conv. | MA Eff. | MA + MAA | |
| iC4= | Steam | Bath | Peak | Sec. | % | % | Yld % | STY g/l-hr |
| 3.0 | 36.9 | 363 | 394 | 1.21 | 90.3 | 76.6 | 69.4 | 247 |
| 3.0 | 36.8 | 379 | 419 | 1.16 | 94.0 | 76.1 | 72.3 | 252 |
| 3.1 | 37.1 | 389 | 397 | 1.22 | 93.7 | 73.2 | 71.1 | 246 |
| 3.1 | 37.0 | 392 | 422 | 1.17 | 94.7 | 69.0 | 66.5 | 263 |

When the pH of the final slurry is too high the catalyst appears to lose selectivity after relatively few hours of operation.

EXAMPLE XV

This Example illustrates the different combination of properties exhibited by a present invention catalyst in comparison with a prior art type of catalyst for selective oxidation of propylene.

An 84% $Mo_{12}Co_{4.5}Fe_3Ni_{2.5}Bi_1K_{0.07}P_{0.5}O_x$/16% $SiO_2$ catalyst was prepared substantially in the manner described in U.S. 3,778,386 (identified as Catalyst P-A below).

An 84% $Mo_{12}Co_{4.5}Fe_3Ni_{2.5}Bi_1K_{0.7}P_{0.45}O_x$/16% $SiO_2$ catalyst was prepared in accordance with the present invention (identified as Catalyst A below).

| Run | Catalyst | Bath Temp. °C. | Propylene Conversion | Acrolein Efficiency | Yield of Acrolein + Acrylic Acid |
|---|---|---|---|---|---|
| 1 | P-A | 351 | 96.2% | 73.6% | 82.2% |
| 2 | A | 351 | 97.6 | 74.5 | 84.9 |
| 3 | A | 355 | 96.8 | 76.2 | 87.0 |

In Run 1, 17.82 grams of 20-30 mesh catalyst (calcined in $O_2$ at 540° C.) were utilized. The propylene was fed at 40 cc/min, the air at 400 cc/min and the water (liquid) at 0.15 cc/min. The contact time in the oxidation reaction zone was 1.7 seconds, and the pressure of the system was 30 psig.

In Run 2, 17.1 grams of 20-30 mesh catalyst (calcined in $O_2$ at 540° C.) were utilized. The propylene feed rate was 40 cc/min, the air feed rate was 400 cc/min, and that of the water (liquid) was 0.15 cc/min. The contact time in the reaction zone was 1.6 seconds, and the pressure of the system was 30 psig.

In Run 3, 18.0 grams of 20-30 mesh catalyt (calcined in $O_2$ at 540° C.) were utilized. The propylene feed rate was 40 cc/min, the air feed rate was 400 cc/min, and that of the water (liquid) was 0.15 cc/min. The contact time was 1.7 seconds, and the pressure of the system was 30 psig.

In comparison with prior art catalysts, the present invention catalysts consistently exhibit a superior ability to enhance the conversion of olefinically unsaturated hydrocarbon to the corresponding aldehydes with a high rate of conversion (at least 95) a high selectivity efficiency to aldehyde product (at least 70 percent). Further, the present invention catalysts have exceptionally stable catalytic activity when subjected to long term continuous conversion of olefinically unsaturated hydrocarbons to aldehydes under vapor phase oxidation conditions.

What is claimed is:

1. A process for preparing an oxidation catalyst corresponding to the formula:

$$Mo_{12}Co_{1-7}Fe_{1-6}Ni_{1-6}Bi_{0.3-3}L_{0.55-2}M_{0.3-0.6}O_x$$

wherein Mo, Co, Fe, Ni, Bi and O are respectively the elements of molybdenum, cobalt, iron, nickel, bismuth and oxygen; L is at least one element selected from potassium and rubidium; M is at least one element selected from phosphorus, cerium, germanium, manganese, niobium, antimony and tantalum; and x represents the number of oxygen atoms between about 35 and 75 sufficient to satisfy the valence requirements of the other elements; said process consisting essentially of the steps of (1) admixing and slurrying in an aqueous medium respectively compounds of Mo, Co, Fe, Ni, Bi, L and M which are at least partially water-soluble, (2) adjusting the final pH of the aqueous slurry admixture within the range between about 1-5, (3) concentrating the aqueous slurry admixture by water removal to yield a catalyst coprecipitate, (4) heating the catalyst coprecipitate at a temperature in the range between about 200°-250° C. in the presence of molecular oxygen, and (5) calcining the catalyst composition at a temperature between about 400°-600° C. in the presence of molecular oxygen.

2. A process in accordance with claim 1 wherein the oxidation catalyst nominally corresponds to the empirical formula:

$$Mo_{12}Co_{4.5}Fe_{2.4}Ni_{2.3}Bi_{0.5-2}K_{0.6-1.4}P_{0.35-0.5}O_x$$

3. A process in accordance with claim 1 wherein the adjustment of final pH in step (2) is within the range between about 1.8-3.6.

4. A process in accordance with claim 1 wherein the step (4) heating of the catalyst coprecipitate is conducted for a period of between about 1-24 hours in the presence of air.

5. A process in accordance with claim 1 wherein the step (5) calcination of the catalyst composition is conducted for a period between about 4 and 20 hours in the presence of air.

6. An oxidation catalyst prepared in accordance with the process of claim 1 which has a binder substrate incorporated therein.

* * * * *